US011052123B2

(12) United States Patent
Mateo Ansón

(10) Patent No.: US 11,052,123 B2
(45) Date of Patent: Jul. 6, 2021

(54) METHOD OF OBTAINING OLIVE OIL AND EXTRACTS FROM OLIVES

(71) Applicant: ISANATUR SPAIN S.L., Puente la Reina (ES)

(72) Inventor: Nuria Mateo Ansón, Saragossa (ES)

(73) Assignee: Isanatur Spain S.L., Puente la Reina (ES)

( * ) Notice: Subject to any disclaimer, the term of this patent is extended or adjusted under 35 U.S.C. 154(b) by 0 days.

(21) Appl. No.: 16/499,396

(22) PCT Filed: Mar. 29, 2018

(86) PCT No.: PCT/ES2018/070281
§ 371 (c)(1),
(2) Date: Sep. 30, 2019

(87) PCT Pub. No.: WO2018/178492
PCT Pub. Date: Oct. 4, 2018

(65) Prior Publication Data
US 2020/0046791 A1 Feb. 13, 2020

(30) Foreign Application Priority Data
Mar. 31, 2017 (ES) ................ ES201700359

(51) Int. Cl.
| | | |
|---|---|---|
| *A61K 36/63* | (2006.01) | |
| *A23L 33/105* | (2016.01) | |
| *A23L 5/30* | (2016.01) | |
| *A23D 9/02* | (2006.01) | |
| *A61K 31/01* | (2006.01) | |
| *A61K 31/047* | (2006.01) | |
| *A61K 31/05* | (2006.01) | |
| *A61K 31/222* | (2006.01) | |
| *A61K 31/355* | (2006.01) | |
| *A61K 31/7032* | (2006.01) | |
| *A61K 31/7048* | (2006.01) | |
| *B01D 11/02* | (2006.01) | |
| *C11B 1/04* | (2006.01) | |
| *C11B 1/10* | (2006.01) | |

(52) U.S. Cl.
CPC ........... *A61K 36/63* (2013.01); *A23D 9/02* (2013.01); *A23L 5/30* (2016.08); *A23L 33/105* (2016.08); *A61K 31/01* (2013.01); *A61K 31/047* (2013.01); *A61K 31/05* (2013.01); *A61K 31/222* (2013.01); *A61K 31/355* (2013.01); *A61K 31/7032* (2013.01); *A61K 31/7048* (2013.01); *B01D 11/0203* (2013.01); *C11B 1/04* (2013.01); *C11B 1/104* (2013.01); *A23V 2002/00* (2013.01); *A61K 2236/15* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS 6,861,083 B2 * 3/2005 Martel .................. A23D 9/00
426/481

FOREIGN PATENT DOCUMENTS

| EP | 2 238 840 | 10/2010 |
|---|---|---|
| ES | 2 051 238 | 6/1994 |
| ES | 2 076 899 | 11/1995 |
| ES | 2 079 322 | 1/1996 |
| ES | 2 136 539 | 11/1999 |
| ES | 2 145 701 | 7/2000 |
| ES | 2 220 090 | 5/2001 |
| ES | 2 172 429 | 9/2002 |
| ES | 2 185 957 | 5/2003 |
| ES | 2 186 467 | 5/2003 |
| ES | 2 194 199 | 11/2003 |
| ES | 2 280 029 | 1/2007 |
| ES | 2 283 191 | 10/2007 |
| ES | 2 311 401 | 2/2009 |
| ES | 2 315 351 | 4/2009 |
| ES | 2 374 675 | 2/2012 |
| ES | 2 392 706 | 12/2012 |
| ES | 2 393 901 | 12/2012 |
| ES | 2 395 032 | 2/2013 |
| ES | 2 401 288 | 4/2013 |
| WO | WO 01/45514 | 6/2001 |
| WO | WO 2006/005986 | 1/2006 |
| WO | WO 2007/042742 | 4/2007 |
| WO | WO 2007/093659 | 8/2007 |
| WO | WO 2013/030426 | 3/2013 |

OTHER PUBLICATIONS

Puertolas E. et al. An overview of the impact of electrotechnologies for the recovery of oil and high-value compounds from vegetable industry: Energy and economic cost implications. Food Research International, 2016, vol. 80, pp. 19-26.

* cited by examiner

*Primary Examiner* — Ralph J Gitomer
(74) *Attorney, Agent, or Firm* — Kolisch Hartwell, P.C.

(57) ABSTRACT

A method comprising the stages of: olive input, separation of the stone from the olive skin and pulp, with the removal of the whole stone; electric pulsing of the olive paste generated in the previous stage, process of dehydration of the pulsed olive paste up to a humidity of less than 30% in a continuous vacuum drying machine and subsequent separation of the oil by centrifugation of the olive oil, followed by dehydration of the degreased pulp up to a humidity of less than 10%; and lastly, application of supercritical fluids ($CO_2$ with or without modifier) to the degreased and dehydrated pulp, under agitation, pressure, temperature and time conditions, obtaining olive extracts and olive flour. The generation of waste, consumption of water, use of highly toxic solvents and loss of the sensory quality of the oil is avoided, the yields improved and the necessary times reduced.

2 Claims, 1 Drawing Sheet

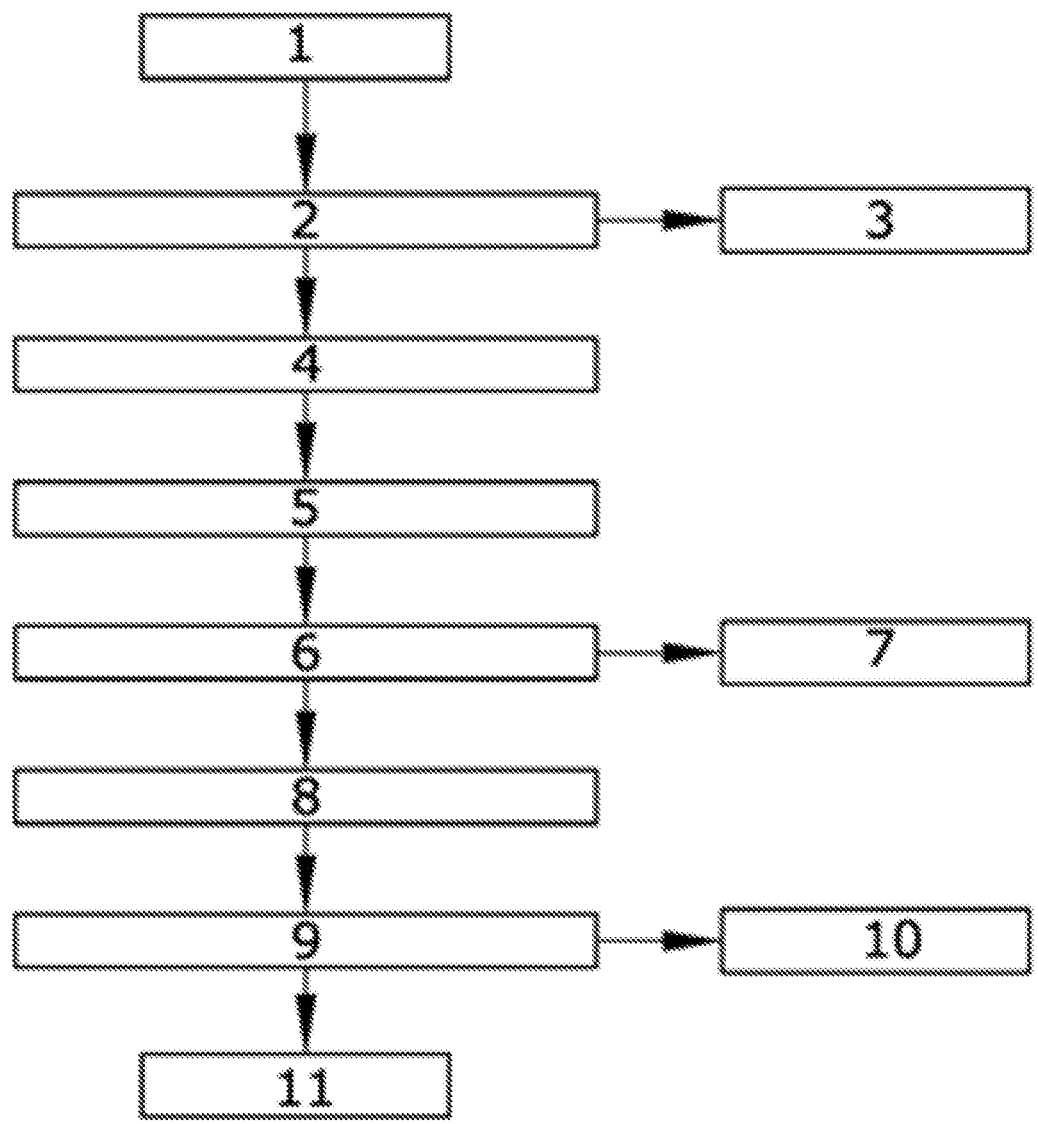

METHOD OF OBTAINING OLIVE OIL AND EXTRACTS FROM OLIVES

CROSS-REFERENCE TO RELATED APPLICATIONS

This application claims priority to ES Patent Application No. P201700359 filed on Mar. 31, 2017, and to PCT Application No. PCT/ES2018/070281 filed on Mar. 29, 2018, the entire contents of which are hereby incorporated by reference.

OBJECT OF THE INVENTION

The object of the present invention is a method for obtaining olive oil, in addition to at least one polyphenol concentrated extract and one functional ingredient that make it possible to maximise the bioactive potential of olives, wherein the products have concentrated active compounds with antioxidant or anti-inflammatory action.

The present invention is characterised by the nature and physico-chemical peculiarities of each and every one of the stages of the method, such that jointly disposed they have a synergistic effect on the final result, which makes it possible to reduce waste, avoid the use of highly toxic solvents, maximise the use of the products, reduce time and improve extraction yields.

To this end, concentration operations are applied that involve removing the stone from the paste and dehydrating it, the resulting product of which is the raw material for obtaining virgin olive oil, extracts obtained applying supercritical fluids ($CO_2$) and a functional ingredient based on olive stone flour with a high concentration of fibre, protein and polyphenol antioxidants.

BACKGROUND OF THE INVENTION

The olive oil industry produces large amounts of waste with low recovery value. The most widely known is pomace or alperujo, depending on whether it stems from a three-phase or two-phase oil extraction system, respectively, which is used to obtain pomace oil. A number of factors cause this process to have a higher environmental impact (1.08 kg $CO_2$ eq/L pomace oil compared to 0.25 kg $CO_2$ eq/L olive oil): transport of large volumes of waste with large amounts of water (60% in alperujo), dried at high temperatures (stage with the highest energy consumption) and emission of $CO_2$ and $N_2$ gases, use of toxic solvents such as n-hexane in the extraction and consequent evaporation and distillation process (with high energy demand), while the oil resulting from that extraction is of lower quality and can hardly compete with other vegetable oils in the market. Although other processes for using these by-products have been described, the present invention focuses on a new method for obtaining virgin olive oil and other derived ingredients following a "zero waste" process that makes it possible to maximise the bioactive potential of olives in a sustainable manner.

The process of the present invention stems from the generation of alperujo, normally generated in the two-phase system, or of vegetation water, in the case of a three-phase system. In addition to being an environmental problem, these waste flows drag active olive compounds with high antioxidant power, such as polyphenols (98% of olive polyphenols are lost), of high value in functional foods. The process of the invention prevents this loss of active compounds by means of dehydration processes under special vacuum conditions and low temperatures, such that the bioactive potential of the olive is preserved and concentrated in the resulting products: olive oil, extracts and functional ingredients.

The invention of the state of the art that relates to the present invention is patent ES2401288 "A method for obtaining olive oil and at least one multifunctional ingredient from olives", specifically to the stoning and dehydration operations, while it is differentiated in subsequent extraction stages that use other methods to preserve the quality of the oil and extracts. These involve extraction using physico-mechanical processes (malaxation and centrifugation) to obtain an olive oil with minimum virgin or virgin extra quality, and a second extraction using supercritical fluids with $CO_2$ to obtain an extract with a high concentration of bioactive compounds from the olive. Additionally, a flour with high fibre, protein and antioxidant polyphenol content is obtained at the end of the extraction processes. The drying process proposed has been improved in order to avoid oxidative processes and to preserve volatile compounds and the organoleptic quality of the oil. Dehydration is only partial (up to 20-30% of humidity) and by applying heat by conduction, not by hot air current, at temperatures below 30-40° C. under negative pressure or a vacuum. Prior to dehydration, the paste is subjected to electric pulses to reduce drying times and increase the yields of oil extraction and bioactive compounds.

Other patents that may relate to the object of the application include:

Patent ES2136539 D2 describes an oil milling method with selective use of olive components, of those intended for obtaining a number of types of olive oil and independent solid components usable for different purposes. The method comprises the following stages: stoning, dilaceration of the olive, peeling or skinning of the dilacerated paste, partial extraction of oil from the de-stoned, dilacerated and skinned olive paste, obtaining olive oil free of olive stones and olive skin; beating of the paste resulting from the partial extractor and centrifugation of the beaten paste, obtaining olive oil by centrifugation. This patent seeks to obtain four different types of olive oil: high-quality oil obtained by cold pressing, oil or lipids from the skin, high-quality oil obtained by centrifugation and olive seed kernel oil.

The described method does not seek the possibility of obtaining extracts and multifunctional ingredients in addition to olive oil. Also, the processes are capable of being improved in terms of yield and times used.

Patent ES2280029 discloses a method for producing olive powder by subjecting the olive-based starting material including the stone to an inactivation stage with oxidase polyphenol and drying the olive paste to remove the water and provide an intermediate product by dry milling.

This method has aspects capable of being improved: on the one hand, not removing the stone negatively affects the sensory quality of the oil obtained, in addition to not improving its oxidative stability and not enabling the extraction of compounds of interest from the stone itself. On the other, both extraction yields and times can be improved.

A number of strategies have also been proposed for recovering valuable olive compounds using very different methods.

Patent ES2186467 describes a method for obtaining antioxidant substances from solutions obtained from the table olive preparation process through the use of solvents. Patent WO2001045514 also describes a method for obtaining antioxidants using an aqueous polar solvent obtained from olives, olive pulp or olive oil. Patent ES2185957 proposes the obtainment of maslinic acid from olive skin using an organic solvent, which entails a previous operation of separating the olive stone and skin from the milling waste containing the stone.

Patent ES2220090 focuses on the recovery of oleuropein from olive vegetation water. To this end, the separation of the stone is proposed to obtain de-stoned olive pulp, which is pressed to obtain a liquid phase. The aqueous phase is separated from the liquid phase, from which oleuropein is obtained. Another patent held by the same company, ES2392706, describes an acid treatment which, applied to the vegetation water, produces hydrolysis of oleuropein to hydroxytyrosol. Patent ES2311401 also addresses the recovery of the hydroxytyrosol from the olive vegetation water using an adequate mixture of solvents. The recovery of all manner of acid compounds, phenols, alcohols and other derivatives from the vegetation water or pomace using solvents and liquid-liquid separation is also proposed, a process patented in ES2051238 equivalent to high-speed countercurrent chromatography.

All the earlier patents generate a liquid phase with an aqueous component (or vegetation water), using solvents in the extraction of compounds of interest, which are recovered from wastewater, vegetation water, olive pulp or whole table olives.

Patent WO2007093659 describes a method for the industrial use of tyrosol and hydroxytyrosol characterised in that it is extracted with solvents from industrial solid by-products of olive milling and that comprises a water-removal phase up to a water content of less than 15%.

Patent ES2194199 describes a process for extracting antioxidants from olives wherein the olives are crushed and dried under the action of a vacuum up to a water content of 1-20%. Said patent claims the obtainment of antioxidant extracts using MCT or alkylene glycol in C2-C6 at temperatures of 110-120° C. and pressures of 40 bar or higher.

Fernandez-Bolaños et al. have proposed another strategy for the complete recovery and revalorisation of olive by-products by combining part of their patented work (2001-2012) [ES2145701; ES2315351; ES2172429; ES2374675; ES2395032]. However, it involves a high-temperature vapour treatment (100-300° C.) and extraction with hexane to degrease or separate the oil from the solid fraction.

The earlier patents apply processes at high temperatures or use solvents that compromise the obtainment of a quality olive oil. They also have aspects capable of being improved, such as the improvement of extraction times and yields.

Other innovative olive oil production systems have been previously patented, which are reviewed below:

Patent EP2238840 describes an olive oil production method that generates oil with enhanced antioxidant properties, higher skin permeability and less olive scent, wherein lactic fermentation is applied to the olive and leaves prior to extraction.

Patent ES2393901, developed by OLEAPURE, describes an innovative method based on "directional sequential compression", recovering the traditional pressing process with the use of a hydraulic press. This process enables the extraction of olive oil and, as a liquid by-product, a vegetable or vegetation water that can be subsequently processed to obtain a concentrated extract of active components.

Patents ES2079322 and ES2076899 describe processes that enable the extraction of oil from de-stoned pomace. In patent ES2079332, once the paste has been separated from the stone it is subjected to a laceration and thermal beating process to carry out separation between the phases using an appropriate system with recovery of by-products for various uses. Patent ES2076899 describes a method for treating the pulp resulting from the extraction of olive oil consisting of subjecting the pulp to a process of separation into stones and fines, wherein fines refers to a mixture of pulp and water from the vegetable matter, a process which is carried out using mechanical means, and subsequently subjecting the fines to the action of a decanter, wherein separation also takes place using mechanical means between the oil and the oil-free residual fines that can be used as feed for animals or fertiliser, while the stones, which can initially be impregnated with pulp, are subjected to the action of an air filter that separates the pulp from the stones, the latter being used as fuel. These two patents have aspects capable of being improved, such as the times used and the yields achieved. Both are based on pomace, from which the stone must be removed, a raw material that is not generated in the method of this patent.

In all the earlier patents there is milling and grinding of the olive that involves breaking the stone. It can be concluded that none of the earlier patents involve the use of dehydrated olive paste as a starting material for extracting virgin or extra virgin quality olive oil. They also have aspects capable of being improved, such as the improvement of extraction times and yields.

Other patents describe the obtainment of concentrated solid olive products other than oil. For example, patent ES2280029 describes the use of material from olives (pomace paste or stoneless alperujo) which is subjected to a stage of inactivation with polyphenol oxidase, scalded at temperatures of 40-250° C., dried to a reduction by weight of 10-40% and subsequent extraction of the oil by means of a press or solvents such as hexane. The resulting product is ground to obtain dry olive powder. Patent WO2006005986, held by the same company as the previous patent, describes a process for obtaining an olive polyphenol concentrate from an olive oil extraction by-product (alperujo, pomace, vegetable water or particulate matter), which comprises extraction by means of a polar solvent, separation by membranes, application of enzymes (conversion of oleuropein to hydroxytyrol or tyrosol), enzyme activation of the polyphenol oxidase at temperatures of 75-100° C., a degreasing stage (which may be earlier) by means of hexane and a final drying stage by vacuum or atomisation to obtain dry powder, which is the concentrate.

Patent WO2007042742 describes a method for obtaining a solid product in the form of powder or fresh paste obtained from "cured" olives, i.e. treated by a combination of alkaline agents and fermentation in brine. The material used is alperujo or pomace which is de-stoned and treated by said method to eliminate the bitterness. The patent extends the application of the process to another type of solid waste, such as pomace waste after extracting the oil using a solvent, olive leaves or table olives.

Patent ES2283191 describes a method for obtaining an olive pulp biomass with a high phenolic antioxidant content through the addition of vitamin E and palmitate ascorbyl and during the olive oil extraction process. However, said obtainment process follows the conventional olive oil extraction method, without previously stoning the olive or applying dehydration operations.

Therefore, the object of the present invention is to develop a method for obtaining olive oil, which also makes it possible to obtain concentrated extracts and additional functional ingredients that overcome the aforementioned drawbacks of waste generation, water consumption, use of highly toxic solvents, loss of the sensory quality of the oil and oxidative stability, wherein times are also reduced and yields improved, in addition to improved preservation of the products obtained by developing a method such as that described below and set out in its essentiality in claim one.

DESCRIPTION OF THE INVENTION

A method for obtaining olive oil, in addition to at least one polyphenol-rich extract for maximising the bioactive potential of the olive, in addition to a functional ingredient.

The method makes it possible to obtain oil from dehydrated olive pulp paste by mechanical means without using solvents in the extraction to obtain virgin olive oil, and other olive products for nutritional and therapeutic purposes using supercritical fluids.

The method comprises the following stages:
1. Separating the stone and skin from the olive pulp using a refining machine equipped with a rotary sieve with a variable pore size of 2-6 mm to let the olive paste pass through.
2. Electric pulsing of the olive paste with an electric field voltage of 1-3 kV/cm, frequency of 114-255 Hz and 2-5 pulses of 50-90 microseconds. The idea is to give the olives an electrical discharge before pressing them. The short impulses of a strong electric field enlarge the pores of the cell membranes, which simplify oil extraction. Pulsing makes it easier to work with completely green olives and no heat, at room temperature.
3. Dehydrating the pulsed olive paste to a humidity of 20-30% in a continuous vacuum drying machine to prevent the deterioration of the antioxidant compounds and loss of volatile compounds, which in a preferred embodiment the vacuum drying conditions can be: vacuum (<80 mbar absolute pressure), temperature (<41° C.) and time (20-100 kg evaporated water/h). To this end, a drying machine specifically designed to dehydrate the product in a continuous process by heat conduction under negative pressures is used.
4. Separating the oil from the olive paste by centrifugation in a decanter with the necessary adjustments to treat de-stoned dehydrated pulp and obtain virgin olive oil.
5. Dehydrating the degreased pulp, after separating the oil, up to a humidity of less than 10% applying under vacuum conditions which, in a preferred embodiment, may be: vacuum (<200 mbar of absolute pressure), temperature (<60° C.) and time (20-100 kg of evaporated water/h).
6. Application of supercritical fluids ($CO_2$ with or without modifier) to the dehydrated and degreased olive paste under agitation, pressure, temperature and time conditions, which in a preferred embodiment may be: specific pressure (150-250 bar), temperature (40° C.) and time (60-240 min) for obtaining an extract characterised by having specific proportions of active olive compounds (squalene, oleuropein, hydroxytyrosol, verbascoside, tyrosol, tocopherol, oleocanthal and other minority compounds. The extract has a therapeutic application against affections involving oxidative stress, inflammation and aterogenic processes, such as cardiovascular and other diseases.
7. The by-product arising from the process, which contains the dehydrated and degreased paste, is an olive flour with a high fibre, protein and polyphenol antioxidant content, which is applied in a percentage of 0.1-5% to bakery products to obtain a product with a high-fibre composition and applicable in functional foods.

With the described method, effects such as the following can be achieved:
Reduced waste, water consumption and wastewater of the oil industry through the application of novel processes.
Avoid the use of highly toxic solvents, such as hexane, in oil extraction processes, which is replaced by mechanical extraction processes (first extraction stage) and sustainable extraction technologies with supercritical $CO_2$ in a second extraction obtainment stage.
Removal of the entire olive stone (without breaking) prior to the separation of the oil to improve the sensory quality of the oil (C5 and C6 volatile compounds) and oxidative stability (the lipoxygenase enzyme in the olive stone is not released) and obtain stone-free pulp, which can be used for other purposes such as cosmetics, extraction of compounds of interest, or other.
Application of electric pulses to the pulp to reduce dehydration times by at least 30% and improve oil extraction yields by at least 3%.
Dehydration to reduce the wastewater, concentrate the compounds of interest in the pulp avoiding the loss thereof and favour the preservation of said product, which is characterised by less water activity than that of the conventional by-products of an olive press (vegetable press, alperujo, pomace).

Unless indicated otherwise, all the technical and scientific elements used in this specification have the meaning usually understood by a person skilled in the art to which this invention belongs. In the practice of this invention, methods and materials similar or equivalent to those described in the specification may be used.

In the description and claims, the word "comprises" and its variants do not intend to exclude other technical characteristics, additives, components or steps. For persons skilled in the art, other objects, advantages and characteristics of the invention will be partly inferred from the description and partly from the practice of the invention.

DESCRIPTION OF THE FIGURES

In order to complement the description being made and with the object of helping to better understand the characteristics of the invention, in accordance with a preferred practical embodiment thereof, said description is accompanied, as an integral part thereof, by a set of drawings where, in an illustrative and non-limiting manner, the following has been represented:

FIG. 1 shows a flow chart wherein the different stages and products obtained throughout the method can be observed.

PREFERRED EMBODIMENT OF THE INVENTION

In view of the FIGURES, a preferred embodiment of the proposed invention is described below.

FIG. 1 shows the flow chart of the method of the invention and which, starting from the olive as raw material (1) has the following stages:
Separating (2) the stone and skin from the olive pulp, obtaining the whole stones (3) on the one hand and, on the other, an olive paste.
Electric pulsing (4) of the olive paste with an electric field voltage of 1-3 kV/cm, frequency of 114-255 Hz and pulses of 50 microseconds; 3.1 kJ/kg.

Dehydrating (5) the pulsed olive paste up to a humidity of 20-30% in a continuous vacuum-drying machine to avoid the degradation of the antioxidant compounds and loss of volatile compounds.

Separating the oil (6) by centrifuging the olive paste, obtaining the oil (7) on the one hand and, on the other, the degreased pulp.

Dehydrating (8) the degreased pulp, after separating the oil, up to a humidity of less than 10%.

Applying supercritical fluids (9) ($CO_2$ with or without modifier) to the dehydrator and degreased olive paste under agitation, pressure, temperature and time conditions obtaining, on the one hand, a series of extracts (10) (squalene, oleuropein, hydroxytyrosol, verbascoside, tyrosol, tocopherol, oleocanthal and other minority compounds) and, on the other, olive flour (11) with a high fibre, protein and polyphenol antioxidant content.

In a more preferred embodiment and as an example of embodiment and never in a non-limiting manner:

700 kg of olives are processed with a refining machine equipped with a sieve having a pore diameter of 4 mm wherefrom 480 kg of de-stoned olive paste are obtained. This paste is subjected to an electric pulse treatment consisting of the application of two 50-microsecond pulses with an electric field intensity of 3 kV/cm and a specific energy of 3.1 kJ/kg of olive paste. The paste is dehydrated in a vacuum (40 mbar of absolute pressure) at a temperature lower than 30° C., obtaining 260 kg of paste with a humidity of 20%. The dehydrated olive paste is subjected to beating at 50 rpm at a temperature of 24-26° C. After 25 min of beating it is centrifuged at 3,500 rpm and 60 kg of oil are extracted. The oil obtained fulfils the virgin olive oil quality parameters, with a degree of acidity less than 0.8%, a peroxide index less than 20 meq, a fatty acid ethyl esters less than 35 mg/kg and K232 and K270 indices below 2.50 and 0.22, respectively. The oil has a total polyphenol content of 0.02% (in gallic acid equivalents), with a concentration of active compounds of 10 mg/kg of hydroxytyrosol (3,4-DHPEA), 11 mg/kg of tyrosol (p-HPEA) and 20 mg/kg of oleuropein (3,4-DHPEA-EA), together with 154 mg/kg of other quantified hydroxytyrosol and tyrosol derivatives (3,4-DHPEA-EDA, 3,4-DHPEA-AC, p-HPEA-EDA), 250 mg/kg of oleocanthal and oleozon, 30 mg/kg of pinoresinol lignan and other phenolic acids and flavones to a lesser extent. After separating the oil, the degreased paste is subjected to a second dehydration under similar vacuum and temperature conditions up to a humidity of less than 10%. This material contains a total of 1.2% of total polyphenols (in gallic acid equivalents), with content of active compounds of 3,770 mg/kg of hydroxytyrosol (3,4-DHPEA), 880 mg/kg of tyrosol (p-HPEA), 1,980 mg/kg of aglycone oleuropein (3,4-DHPEA-EA), 940 mg/kg of verbascoside (derived from hydroxytyrosol), 190 mg/kg of pinoresinol lignan, 2,960 mg/kg of rutin flavonoid and other phenolic acids and flavones to a lesser extent.

130 kg of this dehydrated and degreased paste is subjected to extraction with supercritical fluids, using $CO_2$ with or without ethanol as modifier (5-11%). The extraction conditions are: 250 bar of pressure, 40° C. of temperature, 100 g/min of $CO_2$ flow, 134 kg/kg in a ratio of $CO_2$/input material. After 180 min of extraction time, 45 kg of an oily extract are obtained with a content of 0.2% of hydroxytyrosol, 0.2% of tyrosol and 1.5% of squalene. The concentration of hydroxytyrosol antioxidants and tyrosol is 1,000 times higher than in the pomace oil. The residual solid material after extraction is an olive flour with a total polyphenol content of 5% (in gallic acid equivalents), with a concentration of 0.8% of hydroxytyrosol and 0.8% of tyrosol, and a composition of: 3% of humidity, 12% of protein, 4% of grease (20% saturated, 52% monounsaturated and 28% polyunsaturated), 40% of carbohydrates (31% fibre of which 25% is insoluble and 6% soluble), 10% of ashes.

Olive flour is used to enrich baked cereal products such as breads, biscuits, etc., in concentrations of 1-5% to obtain products with a high fibre content (<6%) and unsaturated greases (>70% of the total fatty acids are unsaturated).

Having sufficiently described the nature of the present invention, in addition to the manner in which to put it into practice, it is hereby stated that, in its essence, it may be put into practice in other embodiments that differ in detail from that indicated by way of example, and to which the protection equally applies, provided that its main principle is not altered, changed or modified.

The invention claimed is:

1. A method of obtaining olive oil and at least one polyphenol extract from olives that each have a stone, skin and pulp comprising:
   separating the stone and skin from the olive pulp of each olive to obtain stones and an olive paste;
   electrically pulsing the olive paste with an electric field voltage of 1-3 kV/cm, a frequency of 114-255 Hz and 2-10 pulses in a range of 50-90 microseconds;
   dehydrating the pulsed olive paste to a humidity of less than 30% in a continuous vacuum drying machine in a vacuum with less than 80 mbar of absolute pressure, a temperature of less than 41° C. and at a rate of 20-100 kg of evaporated water/h;
   degreasing the olive paste by separating the foil from the olive paste using centrifugation;
   dehydrating the degreased olive paste, after separating the oil, at a humidity of less than 10%, applying vacuum conditions of less than 200 mbar of absolute pressure, a temperature of less than 60° C. and a rate of 20-100 kg of evaporated water/h;
   applying supercritical fluids to the degreased and dehydrated olive paste, under agitation, a pressure of 150-250 Bar, a temperature of 40° C. and for a of 60-240 minutes conditions; and
   obtaining from the olive paste, after applying supercritical fluids, extracts and olive flour with a high fiber, protein, and at least one polyphenol antioxidant.

2. The method of claim 1, wherein the separation of the stone and skin from the pulp is carried out by a refining machine equipped with a drive shaft rotary sieve having a variable pore diameter of 2-6 mm to allow the olive paste to pass therethrough.

* * * * *